(12) United States Patent
Hartley et al.

(10) Patent No.: US 8,702,780 B2
(45) Date of Patent: Apr. 22, 2014

(54) ENDOVASCULAR DEPLOYMENT DEVICE

(75) Inventors: David Ernest Hartley, Wannanup (AU); Werner Dieter Ducke, Greenwood (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/074,755

(22) Filed: Mar. 6, 2008

(65) Prior Publication Data

US 2008/0221656 A1 Sep. 11, 2008

Related U.S. Application Data

(60) Provisional application No. 60/905,188, filed on Mar. 6, 2007.

(51) Int. Cl.
*A61F 2/06* (2013.01)
(52) U.S. Cl.
USPC .................................................. 623/1.11
(58) Field of Classification Search
USPC ........ 623/1.11, 1.34; 606/108, 191, 192, 194; 604/96.01, 164.1, 166.01, 264, 508; 604/164.13, 523, 159, 160, 424, 426, 529; 600/431, 435
See application file for complete search history.

(56) References Cited

U.S. PATENT DOCUMENTS

| | | | |
|---|---|---|---|
| 5,429,617 A * | 7/1995 | Hammersmark et al. .... | 604/264 |
| 5,683,451 A * | 11/1997 | Lenker et al. ................. | 623/1.11 |
| 6,102,918 A * | 8/2000 | Kerr ............................... | 606/108 |
| 6,200,338 B1 * | 3/2001 | Solomon et al. .............. | 623/1.34 |
| 6,254,633 B1 * | 7/2001 | Pinchuk et al. ................ | 623/1.3 |
| 6,285,903 B1 * | 9/2001 | Rosenthal et al. ............. | 600/433 |
| 6,520,934 B1 * | 2/2003 | Lee et al. ...................... | 604/103.1 |
| 6,869,417 B1 * | 3/2005 | Walters et al. .............. | 604/164.1 |
| 2002/0029079 A1 * | 3/2002 | Kim et al. ...................... | 623/1.25 |
| 2004/0138734 A1 | 7/2004 | Chobotov et al. | |
| 2004/0193252 A1 * | 9/2004 | Perez et al. .................... | 623/1.23 |
| 2004/0230287 A1 * | 11/2004 | Hartley et al. ................ | 623/1.12 |
| 2005/0148866 A1 | 7/2005 | Gunderson | |
| 2005/0182476 A1 * | 8/2005 | Hartley et al. ................ | 623/1.11 |
| 2006/0004433 A1 * | 1/2006 | Greenberg et al. ........... | 623/1.11 |
| 2006/0116714 A1 * | 6/2006 | Sepetka et al. ................ | 606/200 |
| 2007/0123910 A1 | 5/2007 | Hartley et al. | |

FOREIGN PATENT DOCUMENTS

EP 0 696 447 A2 2/1996

OTHER PUBLICATIONS

PCT/US2008/002997 Int'l Search Report, Sep. 19, 2008.
PCT/US2008/002997 Written Opinion, Sep. 19, 2008.

* cited by examiner

*Primary Examiner* — Thomas McEvoy
*Assistant Examiner* — Jocelin Tanner
(74) *Attorney, Agent, or Firm* — Brinks Gilson & Lione

(57) ABSTRACT

An endovascular delivery device (1) has a portion, such as the nose cone dilator (8), being formed from a radiopaque material and that portion has a selected transverse profile such as a notch (26) so that in a selected rotational orientation of the endovascular delivery device the nose cone dilator can be observed by radiographic means during an endovascular procedure to be in that selected rotational orientation. The selected transverse profile can be a notch, protrusion or aperture. The notch or aperture can be filled with a radio-transparent material to provide a sooth outer surface.

4 Claims, 5 Drawing Sheets

ENDOVASCULAR DEPLOYMENT DEVICE

CROSS-REFERENCE TO RELATED APPLICATIONS

This application claims priority of provisional application Ser. No. 60/905,188, filed Mar. 6, 2007.

TECHNICAL FIELD

This invention relates to a medical device and more particularly to a medical device for endovascular deployment of a prosthesis such as a stent graft within the human or animal body.

BACKGROUND OF THE INVENTION

Minimally-invasive medical procedures are used to deploy prostheses such as stent grafts into the human or animal body. These procedures use a deployment device which is introduced into a vessel such as a blood vessel using the Seldinger technique to deliver a stent graft on the deployment device along a blood vessel to a selected site. A selected site may be a portion of the human or animal vasculature which is damaged or ruptured and the procedure is arranged to deploy a stent graft, effectively a tubular body, across the damaged portion of the vasculature to provide an alternative blood flow path.

In many cases it is not only important to get the longitudinal position of a stent graft in the vasculature in the correct position but it is also important to be able to place the stent graft accurately in a rotational position.

During advancement of a delivery device through the vasculature it is often necessary for the physician to rotate the delivery device to encourage the nose cone dilator at the proximal end of the device to track a previously inserted guide wire so that by the time the delivery device is at a selected position in the vasculature the exact rotational position of the device may not be fully known.

Knowledge of the rotational position is particularly useful for instance for when there is a branch vessel and the stent graft is to be placed so that the branch vessel is not occluded. The stent graft may for instance have a side arm which extends to the branch vessel or a fenestration or scallop which must be correctly placed in the rotational as well as longitudinal position to avoid exclusion of the side arm.

In general delivery devices are constructed with as plain a cross section as possible, such as a circular cross section, to provide minimal obstruction during advancement of a delivery device through the vasculature and damage to the vasculature of a patient during the procedure.

It is the object of this invention to provide a endovascular delivery device with a relatively simple arrangement which will enable a physician to determine the rotational position of a delivery device and hence a stent graft carried on the delivery device.

Throughout this specification the term distal with respect to a portion of the aorta a deployment device or a prosthesis means the end of the aorta deployment device or prosthesis further away in the direction of blood flow from the heart and the term proximal means the portion of the aorta deployment device or end of the prosthesis or stent graft nearer to the heart. When applied to other vessels similar terms such as cordal and cranial should be understood.

SUMMARY OF THE INVENTION

In one form therefore although this may not necessarily be the only or broadest form the invention is said to reside in an endovascular delivery device comprising a part thereof being formed from a radiopaque material and the part being of a selected transverse profile whereby in a selected rotational orientation of the endovascular delivery device the part can be observed by radiographic means during an endovascular procedure to be in that selected rotational orientation.

It will be seen that by this arrangement a portion of the delivery device which goes inside the patient during the endovascular procedure and therefore cannot be directly observed has a profile which can be observed by radiographic techniques from external of the body so that the delivery device and therefore a stent graft or other device carried on the delivery device can be correctly positioned.

Correct positioning may ensure that a scallop on a stent graft for instance is placed in such a way that it does not occlude a blood vessel or a side arm is correctly aligned with respect to a branch blood vessel.

Preferably the selected profile is transversely offset from the longitudinal centre of the part.

The selected profile can be selected from a lateral protrusion, a V-shaped notch or a U-shaped notch on the part. It will be noted that each of these selected profiles are such that they can only be completely observed when the part is in the desired rotational position. A few degrees of rotation off the desired position and they cannot be fully observed. The invention is not, however restricted to these profiles.

Where the selected profile is a notch or a aperture through the part of the delivery device the notch or aperture may be filed with a radio-translucent material so that the part provides a smooth outer surface for passing through the vasculature but at the same time allowing for radiographic observation of the notch.

Preferably the part of the endovascular delivery device which is of the selected profile is a nose cone dilator and the selected profile comprises a transverse notch in the nose cone dilator.

The nose cone dilator may be formed from a material selected from the group comprising vinyl radiopaque thick wall dilator tubing or urethane radiopaque tubing.

The nose cone dilator can comprises a longitudinal groove to receive an indwelling catheter therein and the transverse notch can be at the proximal end of the longitudinal groove. The placement of the notch at the proximal end of the longitudinal groove will enable a physician to ascertain the longitudinal as well as rotational position of the indwelling catheter before the catheter is exposed.

Alternatively the part of the endovascular delivery device which is of the selected profile is a delivery catheter and the selected profile comprises a transverse notch in the delivery catheter.

In an alternative form the invention is said to reside in an endovascular delivery device comprising a delivery catheter, a guide wide catheter extending through and proximally of the delivery catheter, a nose cone dilator at the proximally end of the guide wire catheter and a handle at the distal end of the delivery catheter, at least the nose cone dilator being formed from a radiopaque material and the nose cone dilator being of a selected profile whereby in a selected rotational orientation of the endovascular delivery device the nose cone can be observed by radiographic means during an endovascular procedure to be in that selected rotational orientation.

BRIEF DESCRIPTION OF THE DRAWINGS

This then generally describes the invention but to assist with understanding reference will now be made to the accompanying drawings which show preferred embodiments of the invention.

In the drawings.

DESCRIPTION OF PREFERRED EMBODIMENTS

Figure 1:
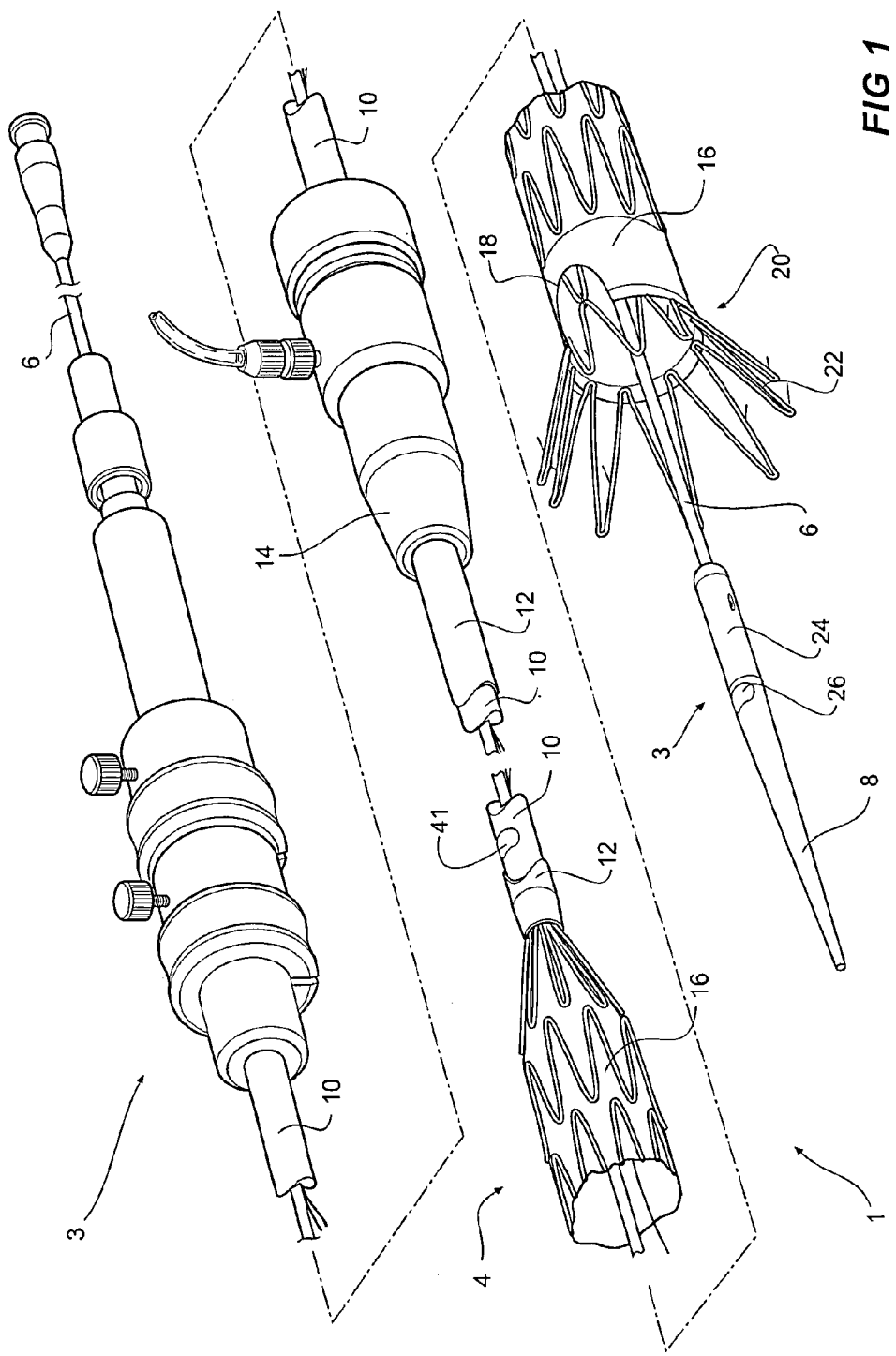
FIG. 1 shows a general view of an endovascular delivery device incorporating one embodiment of the present invention.

FIG. 1 shows one embodiment of endovascular delivery device incorporating the present invention. The delivery device 1 includes a handle portion 3 which in use is intended to remain outside a patient and a delivery portion 4 which is advanced into a patient via the vasculature of the patient. The delivery device includes a guide wire catheter 6 which extends from the handle to a nose cone dilator 8 at the proximal end of the delivery device. Extending from the handle 3 is a pusher catheter 10. A sheath 12 extends from a sheath manipulator 14 on the pusher catheter 10 and during the introduction and advancement of the delivery device into a patient the sheath is advanced to the nose cone dilator 8. As illustrated in FIG. 1, however, the sheath 12 has been withdrawn to expose a stent graft 16 carried on the delivery device.

The stent graft 16 includes a scallop 18 at its proximal end 20 and it is important when the stent graft is delivered that this scallop be in a position so that it does not occlude a side branch artery such as a renal artery. The stent graft is mounted for deployment onto the delivery device with the exposed proximal stent 22 received in a capsule 24 at the distal end of the nose cone dilator 8 and hence the scallop on the stent graft is at a known rotational position with respect to the nose cone dilator when the stent graft is mounted onto the delivery device.

To ensure that the delivery device and particularly the proximal end is at the selected rotational position when the stent graft is to be released within the human or animal body there is provided a transverse notch 26 on the nose cone dilator 8. The nose cone dilator 8 is made from a radiopaque material or is a plastics material or urethane material filled with a radiopaque filler so that when viewed in profile at the selected orientation the notch 26 can be seen.

The pusher catheter 10 also includes a transverse notch 41 at its proximal end adjacent to where the distal end of the stent graft 16 is releasably mounted to the pusher catheter 10. If the stent graft 16 includes, for instance, a bifurcation at its distal end then by knowing where the bifurcation is with respect to the mounting of the stent graft onto the pusher catheter and the rotational position of the pusher catheter by radiographic observation of the notch 41 then the bifurcation may be correctly placed. During delivery the nose cone dilator 8 may be rotated separately than the delivery catheter 10 and so it is useful to separately know the orientation of the delivery catheter 10.

Figure 2:
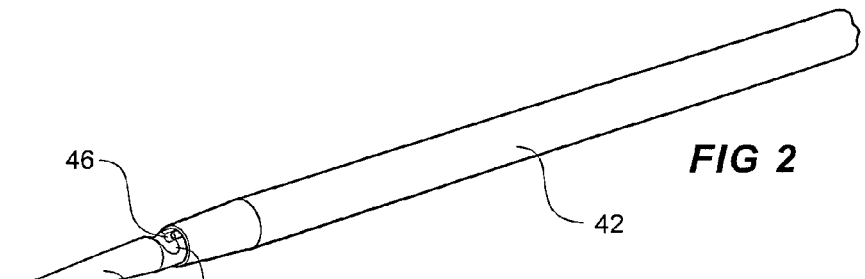
FIGS. 2 and 2A shows detail of a portion of an endovascular delivery device incorporating a radiographically observable profile according to the present invention and with a sheath of the delivery device withdrawn to expose an indwelling catheter.
Figure 2A:
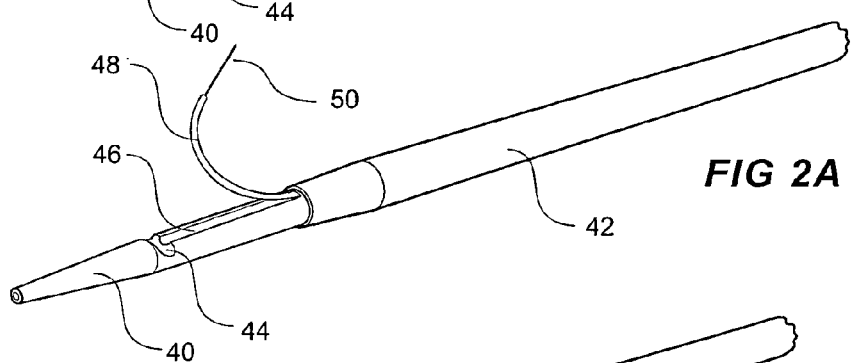
Figure 3:
FIGS. 3 and 3A shows detail of a portion of an alternative endovascular delivery device incorporating a radiographically observable profile according to the present invention and the nose cone in profile showing the observable profile.

FIG. 2 shows the proximal end of an alternative embodiment of endovascular delivery device according to the present invention. In this embodiment the endovascular delivery device includes a nose cone dilator 40 and a sheath 42 extending to the nose cone dilator. The nose cone dilator includes a transverse notch or groove 44 and as can be seen in FIG. 2A a longitudinal notch 46. An indwelling catheter 48 is received in the longitudinal groove 46 and when the sleeve 42 is advanced up to the notch 44 as shown in FIG. 2 the indwelling catheter 48 is received in the groove and terminates just distal of the notch. When the sleeve 42 is retracted as shown in FIG. 3 the indwelling catheter 48 may extend out so that a guide wire 50 can be extended from it to be snared. In this embodiment the transverse notch 44 also assists the physician with determining the longitudinal position of the proximal end of the indwelling catheter.

U.S. patent Ser. No. 10/600,655 entitled "Stent Graft Introducer" describes curved indwelling catheters in deployment devices and the teaching therein is incorporated herein its entirety.

Figure 3A:
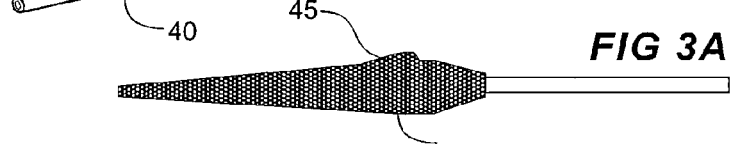

FIGS. 3 and 3A shows detail of a portion of an alternative endovascular delivery device incorporating a radiographically observable profile according to the present invention and the nose cone in profile showing the observable profile. The device shown in FIGS. 3 and 3A is substantially similar to that shown in FIG. 2 and the same reference numerals are used for similar items.

FIG. 3 shows the proximal end of an alternative embodiment of endovascular delivery device according to the present invention. In this embodiment the endovascular delivery device includes a nose cone dilator 40 and a sheath 42 extending to the nose cone dilator. The nose cone dilator includes a laterally extending protrusion 45. As can be seen in the simulated radiographic profile of FIG. 3A the laterally extending protrusion 45 can be distinctly seen so that a physician will be able to easily ascertain the rotational position of the nose cone dilator and hence a device carried on the delivery device.

Figure 4:
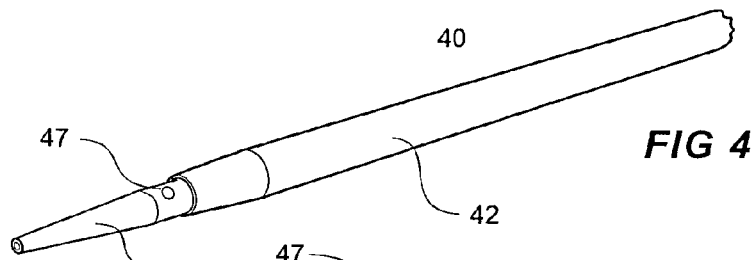
FIGS. 4 and 4A shows detail of a portion of an alternative endovascular delivery device incorporating a radiographically observable profile according to the present invention and the nose cone in profile showing the observable profile.
Figure 4A:
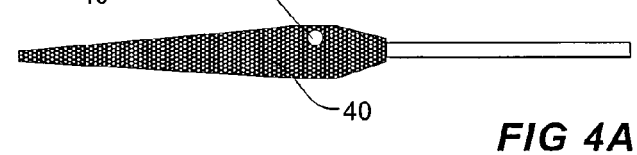

FIGS. 4 and 4A shows detail of a portion of an alternative endovascular delivery device incorporating a radiographically observable profile according to the present invention and the nose cone in profile showing the observable profile. The device shown in FIGS. 4 and 4A is substantially similar to that shown in FIG. 2 and the same reference numerals are used for similar items.

FIG. 4 shows the proximal end of an alternative embodiment of endovascular delivery device according to the present invention. In this embodiment the endovascular delivery device includes a nose cone dilator 40 and a sheath 42 extending to the nose cone dilator. The nose cone dilator includes a laterally offset through aperture 47. As can be seen in the simulated radiographic profile of FIG. 4A the laterally offset through aperture 47 can be distinctly seen so that a physician will be able to easily ascertain the rotational position of the nose cone dilator and hence a device carried on the delivery device. The aperture 47 can be filled with a radio-transparent material to present a smooth outer surface to the nose cone dilator.

Figure 5:
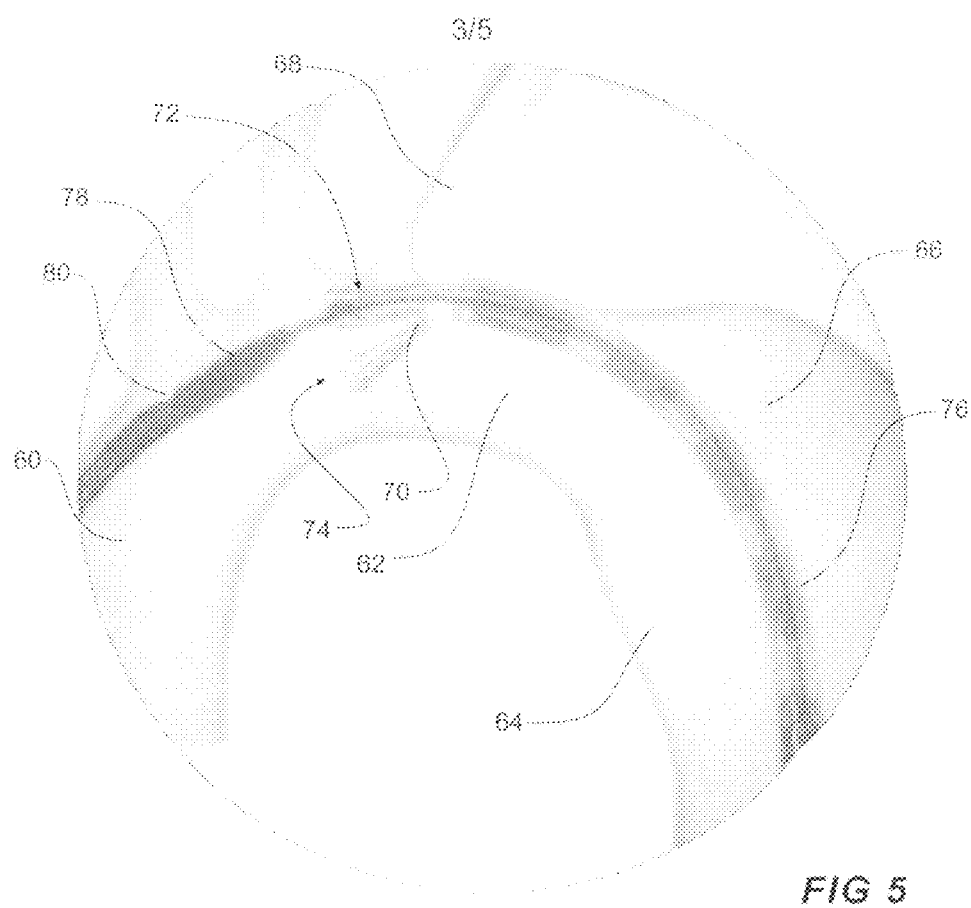
FIG. 5 shows an x-ray photograph of a simulated vasculature of a patient showing particularly the method by which the present invention may be used.

FIG. 5 shows an x-ray photograph of a simulated portion of the thoracic arch of the human vasculature showing part of a procedure for deployment of a stent graft into the thoracic arch of a patient. In this embodiment the thoracic arch includes an ascending aorta 60 an arch 62 and a descending aorta 64. The descending aorta 64 has an aneurism 66 and hence it is desirable to place a stent graft with its proximal end adjacent to the left subclavian artery 68. The stent graft 70 has a scallop 72 at its proximal end 74 and this is too placed so that it extends around the left subclavian artery 68 and does not occlude it. The stent graft delivery device 76 includes a nose cone dilator 78 which has a notch 80 which can be visualized in the x-ray photograph to show that the nose cone dilator is in its desired rotational position. The stent graft 70 is mounted onto the delivery device with the scallop aligned with the notch 80 so that when the notch 80 is in the selected rotational position then the scallop 72 will also be in the selected rotational position.

It will be noted that the scallop in the stent graft is not easily recognizable in the partially constricted form and hence to have a separate radiographic indication by use of the notch 80 facilitates the correct placement of the stent graft with the scallop in the correct place.

Figure 6:
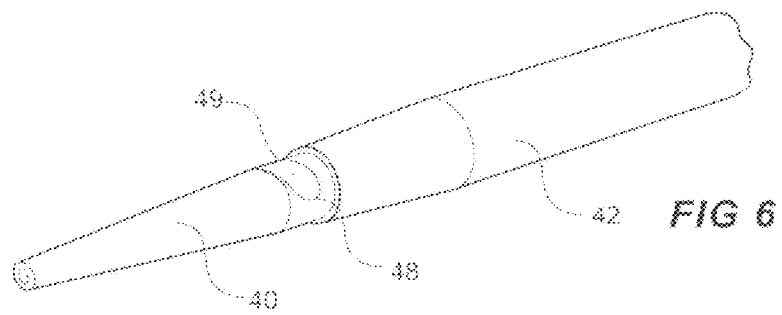
FIG. 6 shows detail of a portion of an endovascular delivery device incorporating an alternative embodiment of a radiographically observable profile according to the present invention.

FIG. 6 shows the proximal end of an alternative embodiment of endovascular delivery device according to the present invention. The device shown in FIG. 6 is substantially similar to that shown in FIG. 2 and the same reference numerals are used for similar items. In this embodiment the endovascular delivery device includes a nose cone dilator 40 and a sheath 42 extending to the nose cone dilator. The nose cone dilator includes a transverse notch or groove 48 but the notch or groove 48 is filled with a radio-translucent material 49 such that the outer surface provides a smooth surface for passing through the vasculature but at the same time allowing for radiographic observation of the notch.

Figure 7:
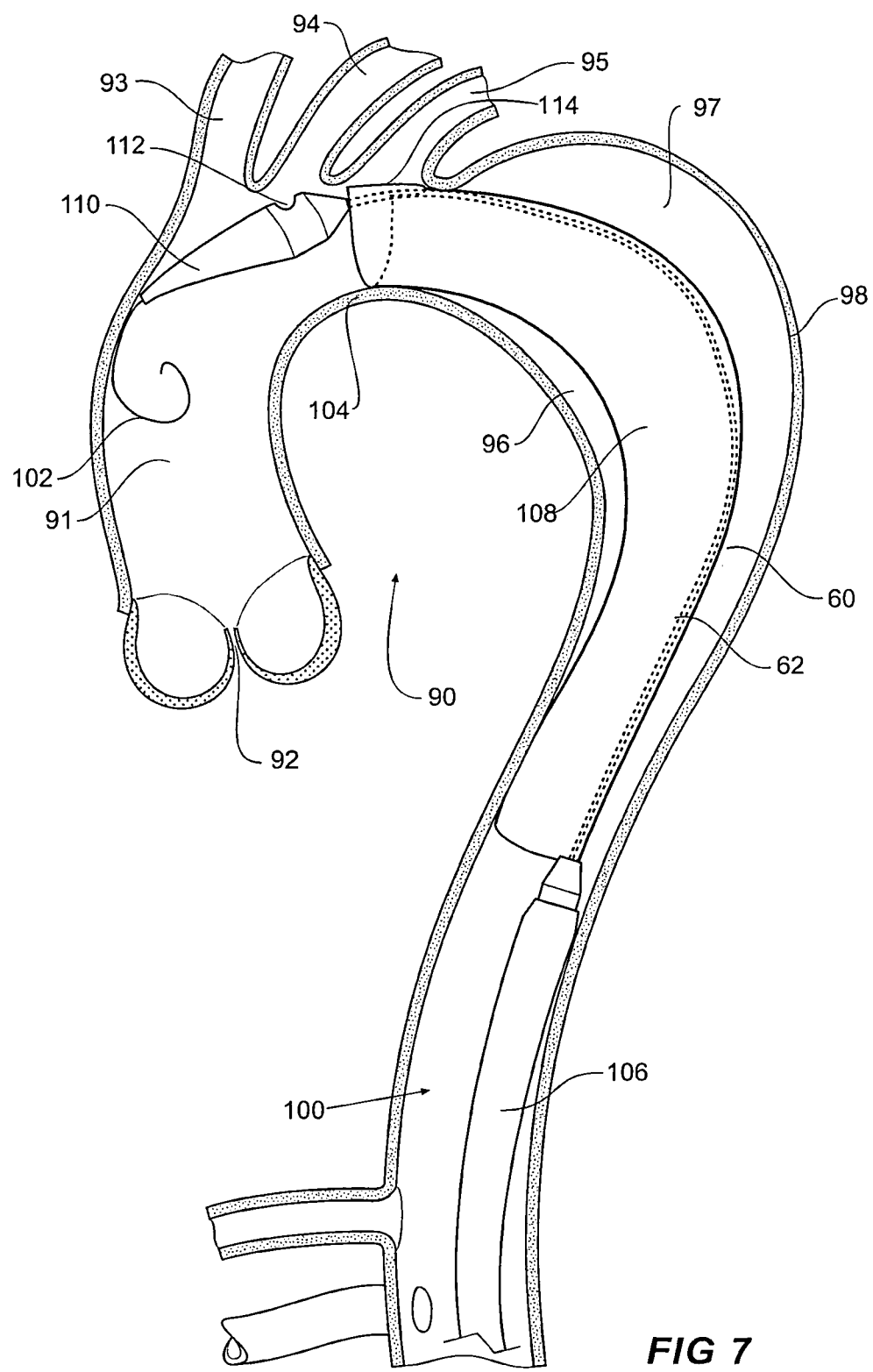
FIG. 7 shows a schematic view of the thoracic arch of a patient with a deployment device incorporating an embodiment of the present invention deployed therein.

FIG. 7 shows a cross sectional view of a thoracic aorta. It will be seen that the thoracic aorta 90 comprises an ascending aorta 91 which receives blood from the heart though an aortic valve 92. At the upper end of the ascending aorta there are branches for the great vessels, the innominate artery 93, the left common carotid artery 94 and the left subclavian artery 95. The aorta after these great vessels is referred to as the descending aorta 96 and it is in this region that a thoracic aortic aneurysm 97 can occur. In a thoracic aortic aneurysm part of the wall 98 of the descending aorta swells and can burst with serious consequences.

As shown in FIG. 7 a deployment device 100 has been deployed up through the descending aorta over a guide wire 102. The proximal end of the deployment device extends over the thoracic arch 104 and into the ascending aorta 91. The sheath 106 has been withdrawn to partially release the stent graft 108 but it is still retained by a release wire system (not shown) onto the deployment device 100. The deployment device 100 has a nose cone dilator 110 at its proximal end and the nose cone dilator has a transverse notch 112. The stent graft 108 has a scallop 114 at its proximal end and the aim of the placement of the stent graft is to ensure that the scallop is positioned to allow blood flow into the left subclavian artery 95. Once the deployment device 100 has been advanced to the position shown in FIG. 6 and before the sheath 106 has been withdrawn the entire device can be rotated until the notch 112 can be seen in profile as shown in FIG. 7 and hence the scallop is in the correct rotational position.

Figure 8:
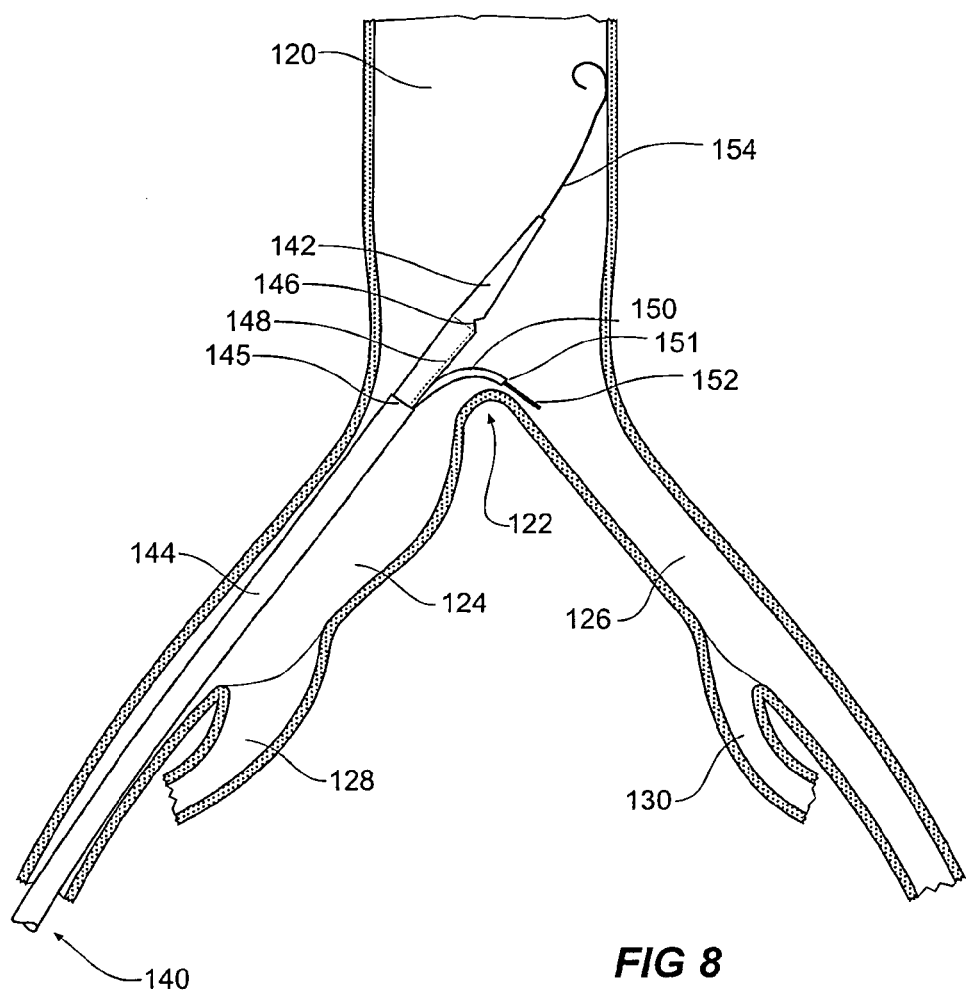
FIG. 8 shows a schematic view of the aortic bifurcation of a patient with a deployment device incorporating an embodiment of the present invention deployed therein.

FIG. 8 shows schematically part of the vasculature of a patient including an aorta 120 extending down to an aortic bifurcation 122 from which extend iliac arteries 124 and 126. An internal iliac artery 128 extends from the iliac artery 124 and an internal iliac artery 130 extends from the iliac artery 126.

An aneurysm in the iliac artery 124 extends along the iliac artery and includes the opening to the internal iliac artery 128 so that for the deployment of a stent graft into the common iliac artery, it will be necessary to have a fenestration or side arm on the stent graft so that an extension piece can be placed into the internal iliac artery 128. The introducer 140 for such a stent graft includes a nose cone dilator 142 and sheath 144. The nose cone dilator 142 includes a V-shaped notch 146. An indwelling catheter 150 is received in a longitudinal groove 148 in the nose cone dilator. The indwelling catheter has a preformed curve at its proximal end but this curve is straightened out when the catheter is covered by the sheath 144. The notch 146 is at the proximal end of the groove 148. The introducer 140 as shown in FIG. 8 has been introduced over a guide wire 154 and positioned so that the nose cone dilator 142 is extending up into the aorta 120 and so that the proximal end 145 of the sheath 144 extends past the aortic bifurcation 122.

The notch 146 in this embodiment has a double function. Firstly it allows the physician to determine the correct rotational position of the introducer 140 to ensure that the curved indwelling catheter when it is released is directed towards the contralateral iliac artery 126. Secondly, when the introducer is in the correct rotational position the physician can determine where the proximal end of the indwelling catheter is positioned longitudinally to ensure that when it is released it will curve towards the contra-lateral iliac artery 126. Too low and the curved indwelling catheter will engage with the aortic wall at the bifurcation and too high and the curved indwelling catheter will engage with the aortic wall above the bifurcation.

In the stage as shown in FIG. 8, the sheath 144 has been partially withdrawn so that the proximal end 151 of the indwelling catheter 150 takes up its original curved shape as discussed above and in particular, the curved proximal end of the indwelling catheter is directed towards the contralateral iliac artery 126.

A guide wire 152 can then be extended from the auxiliary indwelling catheter 150 to extend down the contralateral iliac artery and a snare catheter (not shown) with a snare arrangement at its proximal end can be used to snare the guide wire 152. Subsequent steps of deployment of the stent graft assembly are shown in U.S. patent Ser. No. 10/600,655 entitled "Stent Graft Introducer" mentioned above.

Throughout this specification various indications have been given as to the scope of the invention but the invention not limited one of these but may reside in two or more of these combined together the examples are given for illustration only and not for limitation.

What is claimed is:
1. An endovascular delivery system comprising a longitudinally extending delivery catheter, the delivery catheter comprising a proximal end intended to be introduced into a patient and a distal end intended to remain outside a patient,
   a guide wire catheter extending longitudinally through and extending proximally of the delivery catheter, the guide wire catheter comprising a proximal end,
   a nose cone dilator at the proximal end of the guide wire catheter, a stent graft mounted on the delivery catheter, the stent graft having a proximal edge comprising a scallop, and a distal end, a handle at the distal end of the delivery catheter, at least the nose cone dilator being formed from a radiopaque material and the nose cone dilator comprising an outer substantially cylindrical side surface, a first transverse notch in the outer substantially cylindrical side surface of the nose cone dilator, the first transverse notch being transversely offset from the longitudinal center of the dilator and aligned with the scallop, wherein the first transverse notch does not extend entirely through the side surface of the nose cone dilator, wherein the scallop on the stent graft is at a known rotational position with respect to the transverse notch, a pusher catheter having a proximal end adjacent to the distal end of the stent graft, the pusher catheter including a second transverse notch in a side surface of the pusher catheter, whereby when in use and in a selected rotational orientation of the endovascular delivery device the, nose cone dilator and the first transverse notch can be observed by radiographic means during an endovascular procedure to be in that selected rotational orientation, and an axial and the rotational position of the scallop may be observed by radiographic means, and a separate orientation of the pusher catheter also may be observed;

wherein the nose cone dilator comprises a longitudinal groove on the outer substantially cylindrical side surface thereof to receive an indwelling catheter therein and the first transverse notch is at a proximal end of the longitudinal groove.

2. The endovascular delivery system as in claim 1 wherein the transverse notch comprises a shape selected from a V-shaped notch or a U-shaped notch.

3. The endovascular delivery system in claim 1 wherein the nose cone dilator is formed from a material selected from the group comprising vinyl radiopaque thick wall dilator tubing or urethane radiopaque tubing.

4. The endovascular delivery system in claim 1 wherein the first transverse notch is filled with a radio-translucent material so that the nose cone dilator provides a smooth outer surface for passing through the vasculature but at the same time allowing for radiographic observation of the notch.

* * * * *